United States Patent [19]

Medvinsky et al.

[11] Patent Number: 4,799,999

[45] Date of Patent: Jan. 24, 1989

[54] DYNAMIC PRECIOUS METAL ASSAY METHOD

[75] Inventors: Boris Medvinsky; Leonid Radomyshelsky, both of San Diego, Calif.

[73] Assignee: Tri Electronics Company, Inc., San Diego, Calif.

[21] Appl. No.: 32,366

[22] Filed: Mar. 31, 1987

[51] Int. Cl.$^4$ ............................................. G01N 27/26
[52] U.S. Cl. ................................. 204/1 T; 204/434; 204/406
[58] Field of Search ............... 204/1 R, 1 T, 400, 406, 204/407, 434

[56] References Cited

U.S. PATENT DOCUMENTS

| | | | |
|---|---|---|---|
| 2,531,747 | 6/1947 | Stearn | 204/414 |
| 3,282,804 | 11/1966 | Stearn | 204/1 T |
| 4,179,349 | 12/1979 | Park | 204/400 |
| 4,240,892 | 12/1980 | Riggs | 204/400 |
| 4,376,027 | 3/1983 | Smith | 204/406 |

OTHER PUBLICATIONS

Encyclopeadia Hebraica, pp. 779-786.

Primary Examiner—John F. Niebling
Assistant Examiner—Ben C. Hsing
Attorney, Agent, or Firm—Selwyn S. Berg

[57] ABSTRACT

The invention describes a method for determining the assay of gold alloy. It utilizes a dynamic electrochemical process. The specimen gold is wetted by a described electrolyte, and a small current anodizes the surface of the specimen for a metered period of time. A potential sensing device is then applied to the charged surface, and a potential decay is observed. The potential decay information is compared with empirical data and by interpolating said potential decay with the empirical data a determination of the karat quality of the gold alloy may be determined. This same method may be used for other precious metals, employing different electrolytes, empirical standards, and potentiometers.

5 Claims, 2 Drawing Sheets

DYNAMIC PRECIOUS METAL ASSAY METHOD

BACKGROUND OF THE INVENTION

Though there are many quantitative and qualitative techniques employing the physical and general chemistry to assay precious metals, these are all too sophisticated for most jewelers. For example, a method employed by most jewelers to determine the purity of the gold alloy is to use a series of standard gold pencils and compare the results of a scratch test using said pencils with a gold specimen to be assayed. In such a technique, the jeweler has gold rods of 8 karat, 10 karat, 12 karat, 14 karat, 16 karat, and 18 karat composition and an abrasive stone. He scratches the gold specimen under test on the stone and adjacent to that scratch he scratches the gold pencils on said stone. After treating the stone with an acid and comparing the color of the specimen scratch with the color of the gold pencil scratches, he visually estimates the quality of the specimen in karats. This highly inaccurate system is strongly dependent on the technique and ability of the jeweler employing the test. In contrast, the proposed invention employs the latest electronic devices to make a chemically dynamic test of the purity of precious metals. Operator technique is a minor consideration. The proposed invention uses electro-chemistry in combination with current metering and time dependent circuits in a simple hand-held device. The anode of this electrochemical system is the material under test and the cathode is the reference material. A metered current causes an electro-chemical reaction at the anode and after the current-induced electro-chemical reaction is terminated, the electromotive force is monitored as a function of time. The time dependent decay of the potential difference of the cell so created is indicative of the purity of the precious metals under test. Though the embodiment of the proposed system is to assay gold, it has been determined that the same technique can be used for alloys of other precious metals. The system is self-contained and uses an acid-filled syringe for testing which also contains the reference cathode. Said syringe is wired to control electronics which has appropriate circuitry for accurately metering a current and activating electronic switches to terminate said current and to monitor the potential decay. In addition, the electronics has micro-processors and memory circuits to conveniently operate either an analog or digital display indicating the purity in units of measure familiar to the operator.

SUMMARY OF INVENTION

As mentioned above, this dynamic testing system is amenable to the assay of all precious metals, but the embodiment is directed to the testing the purity of gold. The invention uses an electric cell comprised of a reference cathode of platinum and an anode which is the specimen under test. The electrolyte is a 1½% HCL solution. The electrolyte and the reference cathode is contained in a syringe. A wire is connected to the reference cathode. The syringe has a 2 millimeter diameter hole at its bottom. The bottom of the syringe is placed so the hole contacts the anode specimen in such a manner that the electrolyte wets said anode through the hole. The specimen is wired by means of a clip to the circuitry. After the electrochemical cell is completed by making wet contacts between the syringe and the specimen anode with clip attached to said anode, the circuitry is initiated by pressing a start switch. A current pulse of 3.5 milliamps of about 4 seconds duration is driven into the system at an appropriate voltage level. On a microscopic level, electrons from the current generate ions between the electrodes and cause simultaneous oxidation and reduction to occur on said electrodes. The amount of oxidation and reduction which occurs is a function of the purity of the electrodes. The precious metals are relatively inactive. The elements added to alloy the precious metals are copper, tin and other such metals which are chemically active. When the current pulse is terminated, the ions that are present in the solution is indicative of the electrochemically induced reaction with the specimen anode. The system is now charged up. The electronics then switches from the current mode to a voltage monitoring mode. As shown in FIG. 1, the voltage decays exponentially during the first few seconds to its equilibrium asymptote. FIG. 1 shows the curves for gold of particular purities. The upper curve, curve number 1, shows the dynamic behavior for gold with a higher purity than for the gold in curve number 2. By sampling the voltages as a function of time and comparing the potential values and the slope of the voltage decay versus time with an electronic look-up table, a microprocessor can interpolate the decay curves to evaluate the percentage of gold in the specimen and display its evaluation in units of karats. Because of the critical interdependence of the current pulse and the electronic look-up tables, it has been determined that a current level in the range of 3 to 4 milliamps will produce voltage curve for high purity gold which decays from 5 volts to 1.4 volts and a voltage curve for low purity gold which decays from 0.7 volts to 0.2 volts. The current pulse is maintained for about 3.5 seconds. The test probe, shown in FIG. 2 comprises a syringe of glass or plastic. When the plunger of the syringe is depressed, a drop of electrolyte acid emerges from the tip to wet the test sample and complete the cell. The fundamental control and measuring circuits are block diagrammed in FIG. 3. FIGS. 4 and 5 are modifications of FIG. 3. There is a start button which resets all the circuits and initiates the timer. There is a timer that controls the current pulse. A current generator limits the value of the current. When the current pulse is terminated, a timer monitors the voltage decay. There are Sample and Hold circuits which work in conjunction with the analog to digital voltage converter. The analog to digital voltage converter has an output which is compared with memory, and a microprocessor interpolates the result. The interpolation is then fed into the digital display system which displays the assay of the material.

Because this a dynamic testing system with many variables, the memory information must be obtained empirically for each precious metal. An asymptotic test point at about 1 second after the current pulse has been terminated has been determined for several materials relative to a platinum cathode which is shown in table 1 below. It is also possible increase the accuracy by using several referenced points.

TABLE I

| SILVER or GOLD PLATING | 250 to 380 |
|---|---|
| 6-7 Kt. | 420 to 460 |
| 8 Kt. | 470 to 515 |
| 9 Kt. | 520 to 560 |
| 10 Kt. | 570 to 610 |
| 11 Kt. | 615 to 630 |
| 12 Kt. | 635 to 660 |

TABLE I-continued

| | |
|---|---|
| 13–14 Kt. | 680 to 830 |
| 14 Kt. Plumb | 840 to 870 |
| 18–20 Kt. | 1000 to 1200 |
| Platinum | 1300 to 1400 |

EMBODIMENT

Figure 1:
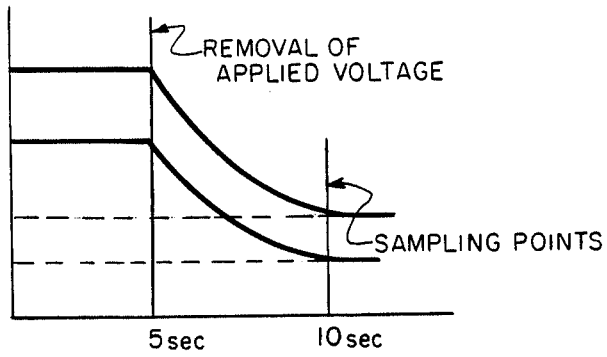
FIG. 1 shows a profile of voltage versus time of the electrochemical cell.
Figure 2:
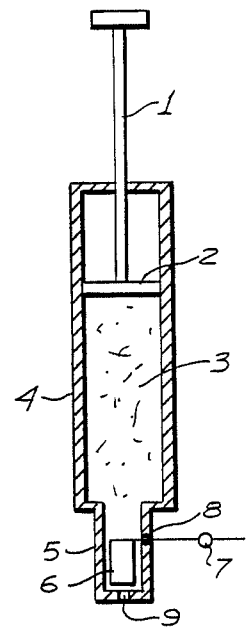
FIG. 2 shows the mechanical parts of the test probe.

The embodiment of a Dynamic Gold Assay Device consists of the test syringe, the specimen anode, and the electronic circuitry. In FIG. 2, the test syringe is illustrated. The test sryinge has a plunger, 1, which is attached to the piston, 2, which is snuggly fitted to the inside diameter of the cylindrical walls, 4, of the test syringe. A 1½% hydrochloric acid solution is used as an electrolyte, 3, which is contained within the cylindrical walls, 4, and the piston, 2, of the plunger. At the lower end of the syringe is the cathode half-cell, 5. The half-cell is shown to have a reduced diameter cylindrical wall and to contain a platinum cathode,6, with a wire, 7, attached and penetrating said half-cell wall through a seal, 8, which is impervious to the electrolyte. The platinum cathode, 6, is a thin cylinder of high purity platinum which is approximately 8 millimeters long and about 1 centimeter in diameter. At the bottom end of the syringe there is a hole on axis which serves as a nozzle, 9. The nozzle is about 2 millimeters in diameter. The nominal length of the syringe with the plunger fully depressed is about 10 centimeters, and of such a diameter as to be conveniently held, as one holds a pencil. By a slight depression of the plunger, 1, a small amount of electrolyte, 3, is expelled from the nozzle, 9, to wet a specimen anode. The wire lead, 7, is connected into the electronics to be described later. The specimen anode is also connected to said electronics and the specimen anode, when made wet by the electrolyte which is maintaining a contact through the nozzle with the half-cell, produces an electro-chemical reaction which is monitered by the electronics.

Figure 3:
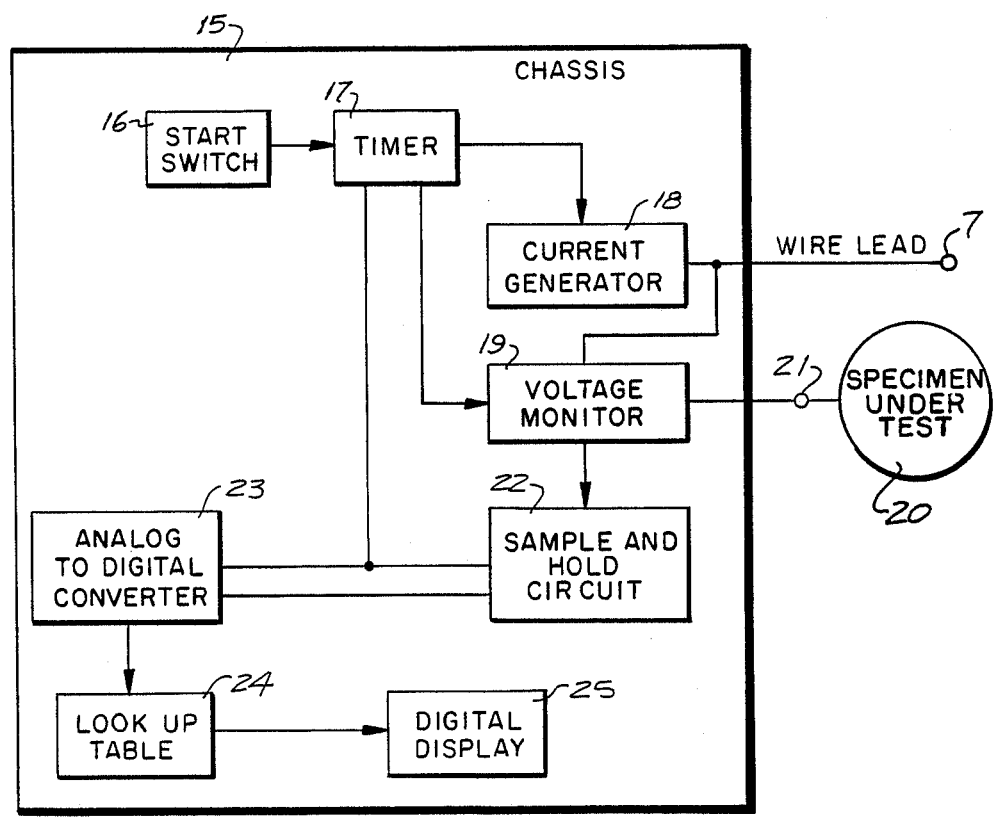
FIG. 3 shows the detailed box diagrem of the circuitry.
Figure 4:
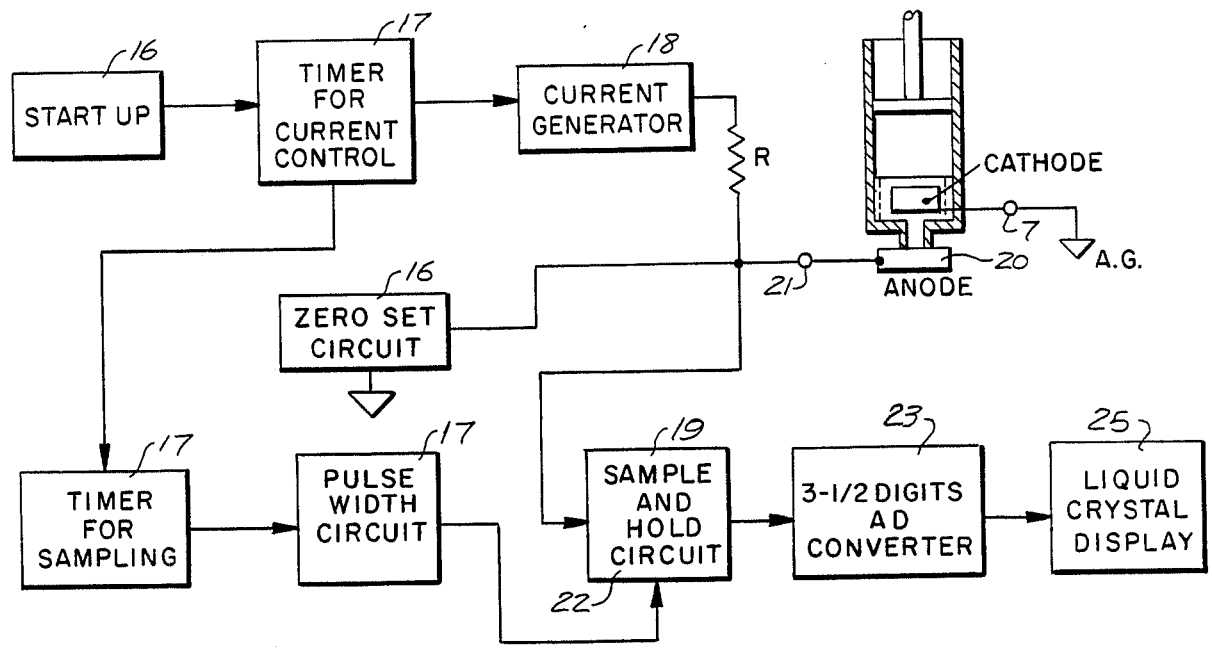
FIG. 4 shows a version of the electronics without logic processing.
Figure 5:
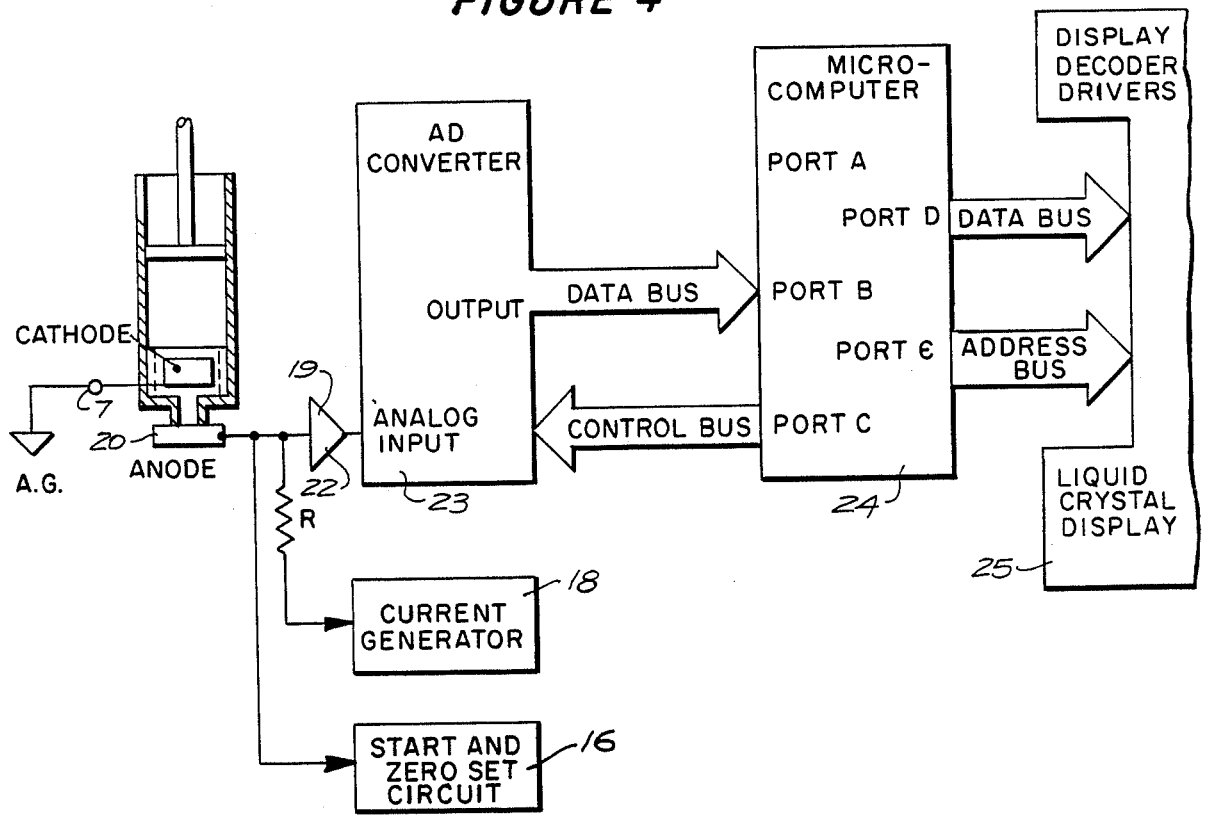
FIG. 5 shows a version of the electronics with logic processing.

FIG. 3 shows a box diagram of the electronics. There are many well known circuits which will generate the functions illustrated in FIG. 3, examples of these are shown in FIGS. 4 and 5. The chassis, 15, contains the circuitry for the invention. There is a start switch, 16, which resets all the circuits and initiates a timer, 17. The timer also contains electronic switches. The timer activates the current generator, 18, which will output a 3.5 milliamp current for 4 seconds. At the end of said 4 seconds, the timer, 17, then initiates the voltage monitor, 19, to follow the aforementioned voltage decay of the specimen under test, 20, in respect to the reference cathode connected to wire lead, 7. The specimen anode is connected to the voltage monitor by a clip lead wire, 21, 1 second after the current pulse was terminated by the timer, 17, a Sample and Hold circuit, 22, opens a window and an analog to digital converter, 23, processes the information through a digital format which may then be compared with information stored in the look-up table, 24. The results of the interpolation that occurs in the look-up table, 24, is transmitted to the digital display, 25. The digital display reads out in some convenient metric.

The circuit referred to as the look-up table, 24, can contain a micro-processor in conjunction with the dedicated memory which not only interpolates, but can also compute time derivatives for comparison with the memory system. By such information processing, both the values of the voltages and the slope of the voltage decay may be used as a dynamic sampling of the electro-chemical reactions. The FIGS. 4 and 5 show different configurations of electronic chassis components which have been produced. FIG. 4 shows a system without a data processing circuit, 24, and FIG. 5 shows a configuration with said logic processing system, 24.

To determine the purity of a gold sample, the specimen is connected to the clip lead wire which goes into the chassis. The nozzle of the test syringe which is also connected to the chassis is placed in contact with the specimen under test. By a slight depression of the plunger a drop of electrolyte is expelled from the nozzle of the test syringe which makes a wet connection of the test specimen into the half-cell within the syringe. The contact of the nozzle to the specimen is maintained while the start switch is depressed. The electronics puts the current switch from anode to cathode for about 4 seconds. The cell is thus charged up by the current pulse and the decay of the potential difference that exists between the anode and cathode is monitored for another 1 second. At the end of the 1 second monitoring period, the asymptodic voltage is compared in a memory device within the chassis and a digital read-out displays the purity of the gold sample under test.

We claim:

1. A dynamic precious metal assay method which comprises the steps of: Introducing an electrolyte onto a sample of precious metal,
    creating a wet junction,
    driving an electric current through said electrolyte,
    anodizing said precious metal,
    terminating said electric current,
    monitoring a potential decay with respect to time of said precious metal sample at said wet junction,
    comparing said potential decay with an empirical table of standards,
    interpolating said potential decay by differentiating against said empirical table of standards, and
    enunciating said interpolation.

2. An introducing method as recited in claim 1, further comprising depressing a plunger of a syringe containing said electrolyte.

3. A comparing method as described in claim 1 further comprising initiating an analog to digital conversion and outputting a signal from said analog to digital converter and storing said signal into a memory.

4. An interpolation method as recited in claim 1 further comprising computing the differences between said potential decay and said empirical standard table.

5. An enunciating method as recited in claim 1, further comprising displaying information on a digital readout.

* * * * *